(12) United States Patent
Meyer

(10) Patent No.: US 6,298,256 B1
(45) Date of Patent: Oct. 2, 2001

(54) DEVICE AND METHOD FOR THE LOCATION AND CATHETERIZATION OF THE SURROUNDINGS OF A NERVE

(76) Inventor: Frank-Egbert Meyer, Merler Ring 135 a, 53340 Meckenheim (DE)

( * ) Notice: Subject to any disclaimer, the term of this patent is extended or adjusted under 35 U.S.C. 154(b) by 0 days.

(21) Appl. No.: 09/394,117

(22) Filed: Sep. 10, 1999

(51) Int. Cl.[7] .................................................. A61B 5/04

(52) U.S. Cl. ..................... 600/373; 600/546; 600/554; 600/557; 607/118

(58) Field of Search ....................... 600/547, 546, 600/554, 373, 378, 548, 557, 461, 464; 607/118

(56) References Cited

U.S. PATENT DOCUMENTS

| 3,682,162 | 8/1972 | Colyer . | |
|---|---|---|---|
| 4,515,168 | * 5/1985 | Chester et al. ................ | 128/741 |
| 5,007,902 | * 4/1991 | Witt ................................ | 604/117 |
| 5,830,151 | * 11/1998 | Hadzic et al. ................. | 600/554 |
| 5,853,373 | * 12/1998 | Griffith et al. ................. | 600/554 |

* cited by examiner

*Primary Examiner*—Linda C. M. Dvorak
*Assistant Examiner*—Daniel M. Ruddy
(74) *Attorney, Agent, or Firm*—Pauley Petersen Kinne & Fejer

(57) ABSTRACT

A device for the location and catheterization of the surrounding area of a nerve of a human or animal body, including a catheter and an electrically conducting puncture needle with proximal and distal ends, which puncture needle forms a continuous lumen with its proximal and distal end open and having an inside diameter which at least corresponds to the outside diameter of the catheter and which, in the region of its proximal end, is equipped with an electrical connecting part for the connection of the puncture needle to an electrical voltage source. At the proximal end, a connecting element with a through-hole communicating with the lumen is provided, onto which an injection tube for the introduction of a liquid through the through-hole into the lumen of the puncture needle is connected, and through the through-hole of which the catheter can be pushed forward into the lumen of the puncture needle all the way to the distal end thereof. Also disclosed is a method for the location and catheterization of the surrounding area of a nerve using such a device.

14 Claims, 2 Drawing Sheets

DEVICE AND METHOD FOR THE LOCATION AND CATHETERIZATION OF THE SURROUNDINGS OF A NERVE

BACKGROUND OF THE INVENTION

1. Field of the Invention

This invention relates to a device for the location and catheterization of the surroundings of a nerve of a human or animal body as well as with a method for the location and catheterization of such a surroundings of a nerve.

2. Description of Prior Art

In surgical processes on the upper and lower extremities, as well as in replantation surgery and pain therapy of a patient, it may be expedient to produce a longer-lasting or continuous blockage of the nerve in the affected area of the human or animal body as well as to maintain this blockade in long-term therapy over a long period of time.

According to conventional methods, a relatively large amount of a local anesthetic for blocking the nerve is required, but this increases the risk of side effects for the patient.

In order to reduce the necessary amount of local anesthetic and its side effects, it is therefore desirable to apply the local anesthetic as close as possible to the surroundings of the nerve to be blocked, so that the desired blocking action of the local anesthetic proceeds satisfactorily, even when a small amount is used. This can be achieved by injection of the local anesthetic directly into the closest surroundings of the nerve to be blocked.

According to the invention, "surroundings of a nerve" is understood to mean optimally the region which is at the smallest possible distance around the nerve to be blocked, but where actual contact with the nerve is excluded.

In this connection, it is known that an electrically conducting metallic needle, which is connected to an electrical voltage source, can be used to locate and search for the nerve to be blocked, in which case the metallic needle is under voltage and serves as an electrode. Using a reference electrode, a stimulating current is given off which is transferred to the nerve to be located and which can be measured by the inserted needle, so that the treating physician is able to locate precisely the nerve to be blocked with the aid of this stimulating current and can guide the needle as close to the nerve as possible, in order to obtain optimum use of the local anesthetic at the nerve, in order to block it.

As soon as the metallic needle serving as an electrode penetrates to the neighborhood of the nerve to be located, a circuit is closed and the nerve is stimulated, which is manifested, for example, in externally visible muscular contractions of the patient.

U.S. Pat. No. 3,682,162 teaches a needle consisting of two concentrically arranged electrodes electrically insulated from one another, which can be connected to an external voltage source and with which the nerve to be located and blocked can be located with the aid of the stimulating current technique described above. A through-hole, arranged in a central area of the central axis of the concentrically arranged electrodes can then be used to introduce a local anesthetic after reaching the immediate surroundings of the desired nerve and applied to it. The known needle has a connection for this purpose at its proximal end, where the syringe, which is known, with the local anesthetic, can be set and then this can be released through the distal end inserted into the immediate surroundings of the nerve.

Especially for providing longer-lasting or continuous nerve blockage as well as for safe long-term therapy, it is necessary to provide a local anesthetic periodically or continuously to the nerve over a long period of time, and, for this, usually a finer catheter is placed all the way to the corresponding immediate surroundings of the nerve to be blocked, but without contacting the nerve mechanically.

For example, it is known from European Patent Publication EP 0102538 that one can first locate the nerve to be blocked with an electrically conducting puncture needle in the manner already described above. Through this puncture needle, the first dose of local anesthetic can be injected through its distal end into the surroundings of the nerve by connecting a syringe at the proximal end (called Single-shot). Therefore, through the puncture needle, a self-retaining canula is pushed into the surroundings of the located nerve to be blocked, the metallic puncture needle serving as guide for the self-retained canula. The puncture needle can be withdrawn from the body while the self-retaining canula remains fixed and lies with its distal end in the surroundings of the nerve to be blocked. Then, it is possible to push a long guide wire through the self-retaining canula into the surroundings of the nerve to be blocked. The self-retaining canula can be removed, having the guide wire remaining in position, and finally the catheter can be pushed forward through the guide wire all the way to the surroundings of the nerve. After removal of the guide wire, the catheter is placed in the surroundings of the nerve to be blocked and serves for the continuous or periodic provision of local anesthetic to the nerve to be blocked.

However, a disadvantage of this known device is, first of all, the complicated structure of the device having a number of individual parts, namely, puncture needle, self-retaining canula, guide wire and catheter, which require highly skilled maneuvering by the operating physician and make the handling unnecessarily difficult. Another problem is that the self-retaining canula to be positioned is usually made of a flexible plastic and, after the metallic puncture needle is removed, it no longer receives guidance, so that unintended movements of the patient could cause a change in the position of the self-retaining canula and then the guide wire, as well as the catheter introduced over it will no longer be in the precise position located with the metallic puncture needle in the surroundings of the nerve to be blocked. This problem increases with increasing depth of the position of the nerve to be blocked within the body, because, with increasing length of introduction or depth of the self-retaining canula, the risk of unintended change of the located position increases. Therefore, the device of the art is suitable for producing blockage of the nerve only in a limited area of application, namely just close to the skin surface, such as in the area of the arm. However this undesirably limits the area of application.

SUMMARY OF THE INVENTION

Therefore, it is one object of this invention to simplify the devices of the art for location and catheterization of the immediate surroundings of a nerve. It is another object of this invention to increase the accuracy and precision with which the catheter is placed at the nerve to be blocked so that even deeper-lying nerve channels and nerves in them can be reached reliably.

These and other objects are addressed by a device for the location and catheterization of the immediate surroundings of a nerve of a human and an animal body comprising a catheter and an electrically conducting puncture needle with a proximal and distal end, which surrounds a continuous lumen open at the proximal and distal end having an inside diameter that corresponds to the outside diameter of the catheter and which is equipped in the region of its proximal end with an electrical connecting part for connection of the puncture needle to an electric voltage source. At the proximal end, a connecting element with a through-hole in communication with the lumen is provided, whereby the injection tube for the introduction of a liquid through the through-hole can be connected in the lumen of the puncture needle and the catheter can be introduced through the through-hole into the lumen of the puncture needle and shifted all the way to the distal end of it.

The device of this invention significantly simplifies handling by reducing the number of individual parts, and a significant improvement in the precision of the introduction of the catheter is achieved. Thus, it is possible to locate the nerve to be blocked with the aid of a stimulating current with the aid of the electrically conducting puncture needle and to search for its immediate surroundings reliably with the distal end serving as an electrode and then to inject a liquid, for example, a local anesthetic, into this immediate surroundings of the nerve with the aid of a connected injection tube connected through a connecting element. By connecting the preferable flexible injection tube, here, undesirable transfer of forces onto the puncture needle inserted into the patient, for example, by pressing on the syringe, is avoided, so that changes in the position of the puncture needle can be prevented.

The injection tube is then removed from the connecting element of the device and, through the hole of the connecting element, the intended catheter can be introduced directly into the lumen of the puncture needle and pushed all the way to the distal end thereof, which lies in the direct surroundings of the nerve.

Thus, the electrically conducting metallic and thus stiff puncture needle is first used as an electrode for locating the nerve and then as a canula for injecting a local anesthetic into the immediate surroundings of the nerve, and finally, as a guide for the catheter to be introduced. The use of other parts, such as self-retaining canulas and/or guide wires and the like can be omitted entirely when using the device according to this invention, so that handling is significantly simpler. At the same time, the guidance of the catheter to be placed is done directly over the puncture needle with which earlier the immediate surroundings of the nerve to be blocked was found with extremely high precision in the known manner using a stimulating current, so that the placement of the catheter is done with very high precision. The puncture needle is pulled out from the body of the patient, but the catheter remains in its position and is located reliably in the immediate surroundings of the nerve to be blocked. Then, through this catheter, for example, with the aid of a pump, a local anesthetic can be introduced periodically or continuously at an extremely low dosage in order to maintain the desired blockage of the nerve over a long period of time.

Since the electrically conducting puncture needle is metallic, for example, steel, as already mentioned, it has a high bending resistance and thus it is especially suitable for searching out deeper-lying nerves to be blocked, whereby even through such a longer puncture needle for deeper-lying nerves, a catheter can be introduced to the located nerve reliably without the danger of undesirable displacements, for example, caused by the movements of the patient.

In accordance with one preferred embodiment of this invention, the puncture needle is coated with an electrically insulating coating on the outside made, for example, of a synthetic material such as polyester or polytetrafluoroethylene. At its distal end, the puncture needle has a ground tip at which the insulating coating is interrupted, so that the puncture needle constitutes a point-like electrode in the neighborhood of the tip of the distal end through which, using a minimal stimulating current, the nerve to be blocked can be located precisely and safely. Paresthesia or even nerve lesions are thus reliably prevented. Because of the close location to the nerve to be blocked, the necessary volume of local anesthetic for reliable blockage of the nerve is reduced even further. Moreover, the latent time to the beginning of the surgery with a nerve blockage in the forefront of a surgical intervention is reduced to a minimum.

As a result of the electrically insulated coating of the puncture needle, such as polyester or polytetrafluoroethylene, a low irritation pyrogen-free and highly smooth coating is produced on the puncture needle. Thus, there are no grinding residues or grainy enclosures on the needle body of the puncture, which otherwise could lead to irritation of the surrounding tissues or cause allergic reactions of the organism.

The polished section of the puncture needle can also be coated in certain areas with the insulating coating, and then only the distal end is free from the insulating coating and can act as a point-like electrode. In such a case, it is possible to carry out the introduction of the puncture needle without any trauma, since surrounding tissue is only displaced instead of being perforated. Such an insertion channel heals rapidly and even sharp puncture needles, for example, with a 15° incline at the tip, can be introduced without any risk, directly without prior puncture.

The connecting element at the proximal end of the puncture needle, to which optionally the injection tube, for the introduction of a liquid such as a local anesthetic, can be connected, or, with the injection tube removed, the catheter can be introduced into the lumen of the puncture needle through the hole, in accordance with one preferred embodiment, a known Luer-lock screw connecting element is used to which a correspondingly designed injection tube with a similar Luer-lock screw connecting element can be screwed on removably, so that standard surgical equipment can be employed.

In order to couple out any possible movements of the connecting element of the puncture needle, which is introduced with the highest precision to the nerve to be blocked, in accordance with one embodiment of this invention, the connecting element is connected with a flexible tube section to the proximal end of the puncture needle, so that movements at the connecting element, for example, during the insertion and/or removal of the injection tube will not be transferred to the distal end of the puncture needle, which is in the surroundings of the nerve, and undesirable displacement of its position can be avoided.

The electrical connecting part of the puncture needle is preferably equipped with an electrically conducting cable for connection to an external voltage source, whereby the device of this invention can be connected to almost any nerve stimulators that are available on the market.

The puncture needle can have a length of, for example, 30 to 150 mm, preferably 50 to 120 mm nominally, as a result of which it can reach deeper-lying nerves within a human and/or animal body.

The method of this invention for the location and catheterization of the surroundings of a nerve of a human or animal body comprises the steps of connecting the injection tube to the connecting part and connecting the puncture needle to a voltage source through the electrical connecting part and then introducing the puncture needle into the body. Subsequently, with the aid of the puncture needle connected to the electrical voltage source, the surroundings of the nerve to be blocked are located with the distal end of the puncture needle as a result of which the nerve is located. A local anesthetic is introduced through the inlet line and through the puncture needle into the surroundings of the nerve. After removal of the injection tube from the connecting part, the catheter is introduced through the free connecting part into the lumen of the puncture needle and, guided by the puncture needle, pushed to the distal end thereof. Finally, the puncture needle is removed from the body leaving the catheter with its distal end in the surroundings of the nerve.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Figure 1:
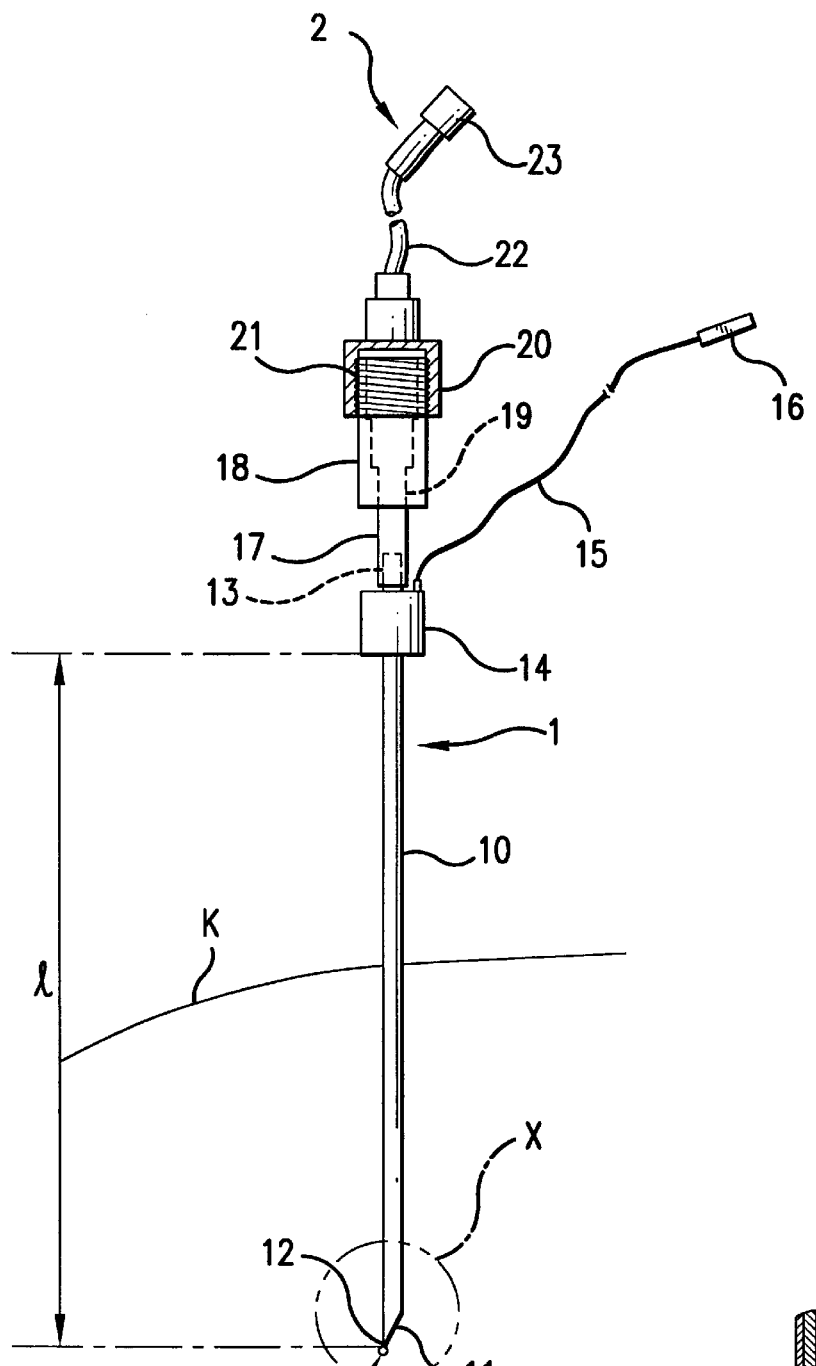
FIG. 1 is a diagram of a device introduced into a body for locating and catheterizing the surroundings of a nerve in accordance with one embodiment of this invention.

FIG. 1 shows a device in accordance with one embodiment of this invention for the location and catheterization of the surroundings of a nerve to be blocked, which is located in position P within body K of a patient. The device comprises a puncture needle 1 with a metallic electrically conducting hollow needle body 10 with distal end 12 and proximal end 13 and an inclined ground surface 11 with an angle of, for example, 15 to 30° formed at the distal end 12.

Figure 2:
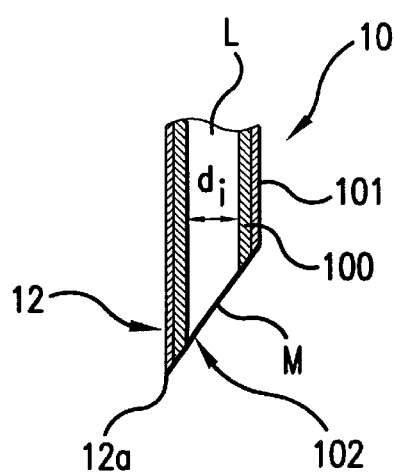
FIG. 2 is an enlarged section of detail X shown in FIG. 1.

As can be seen from the enlarged representation shown in FIG. 2, the hollow needle body 10 comprises a wall 100 having a circular cross-section, which is made, for example, from a steel such as V2A. An electrically insulating coating 101 made of polyester or polytetrafluoroethylene is applied on the outside of wall 100 so that wall 100 is electrically insulated on the outside, but wall 100 itself is completely electrically conducting.

Inside the needle body 10, a lumen L with constant inside diameter di is formed from the proximal end 13 to the distal end 12, is accessible from proximal end 13 as well as from distal end 12 and is surrounded by wall 100.

Furthermore, in the region of the proximal end 13 of puncture needle 1, an electrical connecting part 14 is arranged with electrical wire 15 and connecting sleeve 16 for connection to an outside voltage source, for example, to a commercially available nerve stimulator. The puncture needle 1, that is, its wall 100, can be connected to the electrical voltage source by means of connecting sleeve 16, wire 15 and electrical connecting part 14, and can conduct an electrical current.

The insulation of the electrically conducting wall 100 of needle body 10 with coating 101 acts as a complete outside insulation of puncture needle 1. Only in the area of the ground surface 11 is the tip 12a of the distal end 12 without any coating, so that the area, which is marked with reference number 12a, represents an almost point-like electrode, at which the puncture needle 1 is not insulated and can conduct an electrical current to connecting part 14 and to an electrical voltage source that can be connected to it.

At the same time, however, coating 101 permits nontraumatic introduction of puncture needle 1 into body K.

As an extension of the proximal end 13 of puncture needle 1, with the aid of a flexible tube section 17, a connecting element 18 in the form of a known female Luer-lock screw connecting element with a through-hole 19 is provided, which communicates through tube section 17 with lumen L inside puncture needle 1. In accordance with the embodiment shown in FIG. 1, a flexible injection tube 2 is screwed onto this female Luer-lock screw connecting element 18 and has, for this purpose, on one end, a correspondingly designed male Luer-lock screw connecting element 20 with threads 21 for screwing onto the female Luer-lock screw connecting element 18. With this screw connecting element 20, connected through a tube section 22, at the other end of the injection tube 2, again a female Luer-lock connecting element 23 is formed, to which, for example, a syringe can be connected.

In order to locate and catheterize a nerve or its immediate surroundings, the device thus produced is used as follows:

First, as shown in FIG. 1, the injection tube 2 is connected to connecting element 18 of puncture needle 1 and in the connecting element 23 of injection tube 2, a syringe (not shown) is connected. The syringe can contain, for example, a local anesthetic. Furthermore, the electrical connecting part 14 of puncture needle 1 is connected to an electrical voltage source, preferably a nerve stimulator, not shown, by means of electrical line 15 and sleeve 16. Then, the puncture needle 1 with its distal end 12 is inserted in the known manner into the body which is indicated by K in FIG. 1.

An electrical voltage is applied to puncture needle 1 from the nerve stimulator connected to electrical connecting part 14 in the manner described, and this voltage is tapped at the free distal end 12 of puncture needle 1 at tip 12a, while the rest of the puncture needle 1 is insulated from body K by coating 101. The counter-electrode to the point-like electrode in the area of tip 12a of the distal end 12 of puncture needle 1 is hereby formed by a main electrode on body K, which is not shown here in detail.

When the puncture needle 1 is guided into the neighborhood of the nerve to be located, an electrical current flows through the main electrode (not shown), body K and puncture needle 1 with its electrical connecting part 14 connected to the nerve stimulator, which excites the nerve and produces visible muscle contractions.

With the aid of this almost point-like electrode at the tip 12a of the distal end 12, the position P of the nerve, shown in FIG. I and intended for blockage, is located precisely by pushing the distal end 12 of puncture needle 1 as close to the surrounding of the nerve as possible. A local anesthetic can then be injected through the injection tube 2 connected to connecting element 18 and a syringe connected to the tube, the local anesthetic passing through connecting tube 22 through hole 19 in connecting element 18, tube connecting element 17, the continuous lumen L inside the puncture needle 1, and, finally, to distal end 12 into the immediate surroundings of the nerve, as a result of which a first blockage (single-shot) is achieved.

For long-term blockage, it is preferred to place a catheter with its distal end in the immediate surroundings of the nerve to be blocked, so that a local anesthetic can be introduced over a long period of time.

Figure 3:
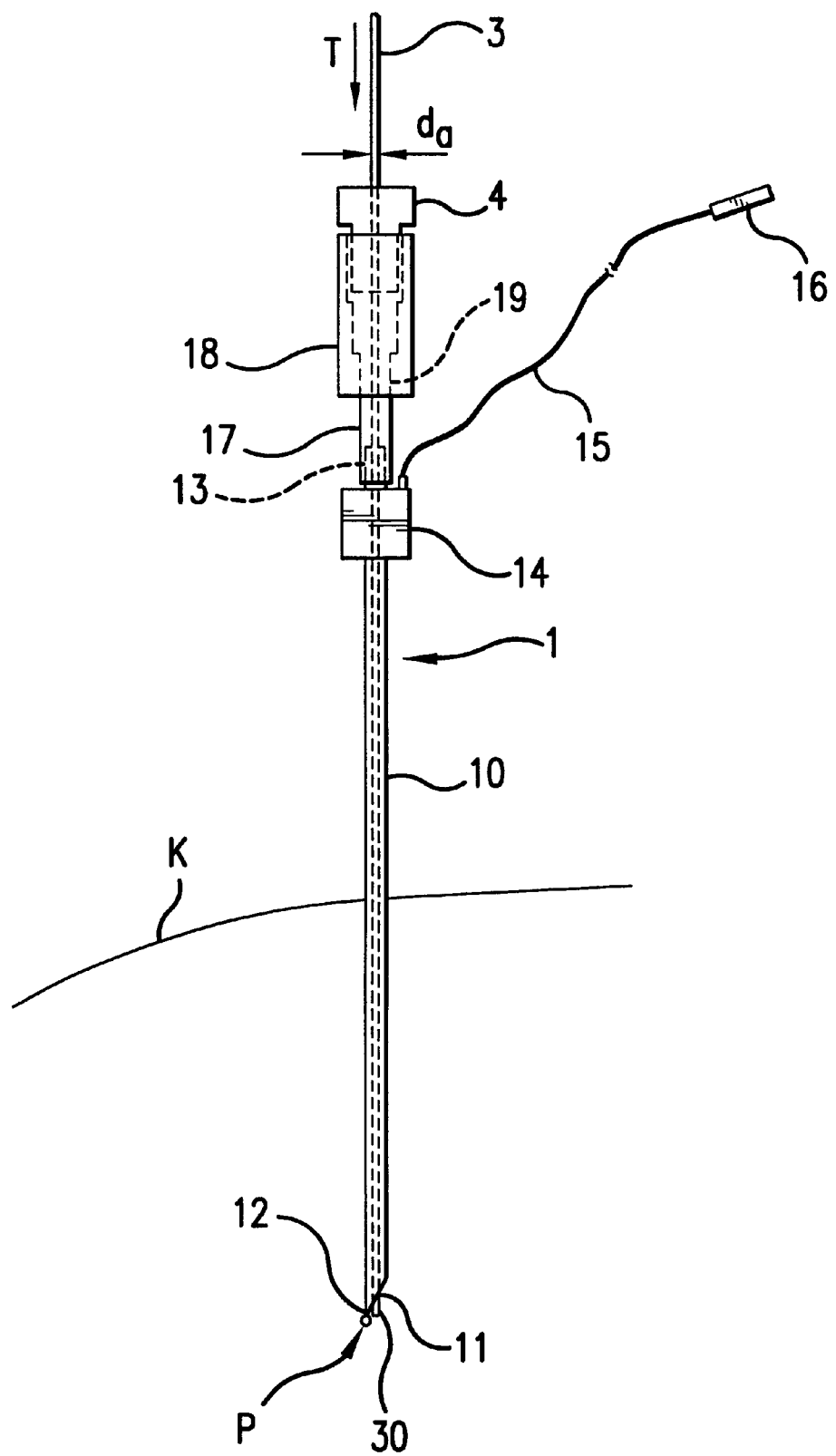
FIG. 3 is a diagram showing the introduction of a catheter through the device in accordance with one embodiment of this invention.

As can be seen in FIG. 3, for this purpose, first with the position of puncture needle unchanged, the injection tube 2 with its screw connecting element 20 is removed from screw connecting element 18 of puncture needle 1, so that the through-hole 19 inside the screw connecting element 18 is accessible from the outside. For example, using a known introduction aid 4, which is inserted into the through-hole 19 of the screw connecting element 18, it is possible to introduce a catheter 3 in the direction of arrow T through the through-hole 19 of the screw connecting element 18 and screw connection piece 17 into the continuous lumen L in the region of the proximal end 13 of puncture needle 1, and, to push it through the continuous lumen L to the distal end 12 of puncture needle 1. For this purpose, catheter 3 is preferably provided with longitudinal markings to enable measurement of the corresponding forward movement all the way to the distal end 12. The forward movement of catheter 3 is made possible by the fact that the continuous lumen L inside puncture needle 1 has an inside diameter $d_i$ which corresponds at least to the outside diameter of catheter 3. Thus, with the guidance of puncture needle 1, catheter 3 is passed through the continuous lumen L all the way to the distal end 12 of puncture needle 1, whereby the distal end 30 of the catheter extends through discharge opening 11 of puncture needle 1. Thus, in a very simple way, catheter 3 can be pushed forward inside puncture needle 1 all the way to the immediate surroundings of the nerve to be blocked in position P, where, prior thereto, the puncture needle 1 had been pushed with high precision with the aid of the electrical stimulating current. Then, the puncture needle 1 is removed from body K in a direction opposite to the direction of arrow T, whereupon catheter 3 remains in the indicated position so that the distal end 30, which forms outlet openings, will lie directly at the nerve to be blocked in position P without ever touching this nerve. Through catheter 3, a local anesthetic can be introduced to the nerve over a long period of time in order to maintain blockage even over a long period of time.

Because the puncture needle 1 is metallic and is thus stiff, it can be used even for a large insertion depth for a nerve which lies correspondingly deeply in body K to provide reliable and highly precise introduction of catheter 3 without the danger of change in the position of the puncture needle 1 as a result of unintended movement of the patient. Therefore, puncture needle 1, for example, with a nominal length of up to 120 mm or more, can be designed in order to be able to reach deep-lying nerves.

What is claimed is:

1. A device for location and catheterization of an area surrounding a nerve of a human or animal body comprising: a catheter (3); an electrically conducting puncture needle (1) having a metallic electrically conducting hollow needle body (10) with proximal and distal ends (13 and 12, respectively), and forming an open continuous lumen (L), from the proximal end to the distal end, having an inside diameter ($d_i$) at least corresponding to an outside diameter ($d_a$) of the catheter; an electrical conducting part (14) at the proximal end (13) connecting the puncture needle (1) to an electrical voltage source; a connecting element (18) connected to the proximal end (13) of the puncture needle (1) and forming a through-hole (19) in communication with the lumen (L); and an injection tubing (2) connected to the connecting element (18) in fluid communication with the through-hole (19) and the lumen (L) of the puncture needle (1), the catheter (3) extending through the through-hole (19) into the lumen (L) of the puncture needle (1) and pushed forward to the distal end (12).

2. A device according to claim 1, wherein the puncture needle (1) is coated with an electrically insulating coating (101) on an outside surface and comprises a ground tip (12*a*) at the distal end (12), said ground tip (12*a*) being uncoated and forming a pointed electrode on the puncture needle (1) in the region of the ground tip (12*a*) of the distal end (12).

3. A device according to claim 2, wherein the electrically insulating coating (101) is a synthetic polymer.

4. A device according to claim 1, wherein the connecting element (18) comprises a Luer-lock screw connecting element and the injection tube (2) is removably screwed onto the Luer-lock screw connecting element.

5. A device according to claim 1, wherein the connecting element is connected to the proximal end (13) of the puncture needle (1) by a flexible tube section (17).

6. A device according to claim 1, wherein the electrical connecting part (14) comprises an electrically conducting cable (15) connected to the electrical voltage source.

7. A device according to claim 1, wherein the puncture needle (1) has a length (I) of about 30 to about 150 mm.

8. A device according to claim 3, wherein the connecting element (18) comprises a Luer-lock screw connecting element and the injection tube (2) is removably screwed onto the Luer-lock screw connecting element.

9. A device according to claim 8, wherein the connecting element is connected to the proximal end (13) of the puncture needle (1) by a flexible tube section (17).

10. A device according to claim 9, wherein the electrical connecting part (14) comprises an electrically conducting cable (15) connected to the electrical voltage source.

11. A device according to claim 10, wherein the puncture needle (1) has a length (I) of about 30 to about 150 mm.

12. A device according to claim 1, wherein the continuous lumen (6) inside puncture needle (1) has an inside diameter ($d_i$) which corresponds to the outside diameter ($d_a$) of the catheter (3).

13. A device according to claim 1, wherein the catheter (3) is provided with a plurality of longitudinal markings suitable for measurement of a corresponding forward movement toward the distal end (12) of the puncture needle.

14. A method for the location and catheterization of the surrounding area of a nerve of a human or animal body comprising: connecting an injection tube (2) to a connecting part (18) of a puncture needle (1) having a metallic electrically conducting hollow needle body (10) with proximal end (13) and distal end (12) and forming an open continuous lumen (6) from the proximal end to the distal end connected to an electrical voltage source; inserting the puncture needle (1) into a body (K) and applying an electric voltage from the electrical voltage source to the puncture needle (1) whereby the surrounding area of the nerve can be determined; injecting a local anesthetic through the injection tube (2) and the hollow needle body (10) of the puncture needle (1) into the surrounding area of the nerve; removing the injection tube (2) from the connecting part (18); introducing a catheter (3) into the lumen (L) formed by the puncture needle (1) and with guidance through the puncture needle (1), pushing the catheter (3) forward to the distal end (12) of the puncture needle (1); and removing the puncture needle (1) from the body (K), whereupon the catheter (3) remains with its distal end (12) in the region of the surrounding area of the nerve.

* * * * *